US008603504B2

(12) United States Patent
Sagawa et al.

(10) Patent No.: US 8,603,504 B2
(45) Date of Patent: Dec. 10, 2013

(54) COSMETIC POWDER

(75) Inventors: Koichiro Sagawa, Kawasaki (JP); Kazuhiko Tobita, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 1645 days.

(21) Appl. No.: 11/392,564

(22) Filed: Mar. 30, 2006

(65) Prior Publication Data

US 2006/0233728 A1    Oct. 19, 2006

(30) Foreign Application Priority Data

Mar. 30, 2005    (JP) ................. 2005-100164

(51) Int. Cl.
*A61K 8/72* (2006.01)

(52) U.S. Cl.
USPC ....... 424/401; 424/59; 424/70.16; 424/70.17; 424/70.12

(58) Field of Classification Search
None
See application file for complete search history.

(56) References Cited

U.S. PATENT DOCUMENTS

| 3,632,744 | A |   | 1/1972  | Paulsen et al.  |         |
|-----------|---|---|---------|-----------------|---------|
| 4,640,943 | A |   | 2/1987  | Meguro et al.   |         |
| 6,034,204 | A | * | 3/2000  | Mohr et al.     | 528/328 |
| 6,555,708 | B1| * | 4/2003  | Yamato et al.   | 562/575 |
| 7,094,462 | B1|   | 8/2006  | Yokoyama et al. |         |
| 7,199,101 | B2|   | 4/2007  | Hatajima et al. |         |
| 2004/0228890 | A1 | | 11/2004 | Blin et al. |      |
| 2006/0067902 | A1 | | 3/2006  | Gotou et al. |     |
| 2006/0233728 | A1 | | 10/2006 | Sagawa et al. |    |
| 2008/0124289 | A1 | | 5/2008  | Kurfurst et al. | |

FOREIGN PATENT DOCUMENTS

| CN | 1370142 A | 9/2002 |
|----|-----------|--------|
| JE | 61-069709 | 4/1986 |
| JP | 51-28610  | 3/1976 |
| JP | 55-167209 | 12/1980 |
| JP | 61-10503  | 1/1986 |
| JP | 62-250074 | 10/1987 |
| JP | 1-180811  | 7/1989 |
| JP | 02-16725  | 1/1990 |
| JP | 02-016725 | 4/1990 |
| JP | 02133497 A * | 5/1990 |
| JP | 5-339126  | 12/1993 |
| JP | 08-81331  | 3/1996 |
| JP | B-3690052 | 6/1998 |
| JP | 10-265761 | 10/1998 |
| JP | 2003-105221 | 4/2003 |
| JP | 2004-099458 | 4/2004 |
| JP | 2004-231564 | 8/2004 |

OTHER PUBLICATIONS

English Abstract, JP 10-265761.*
Office Action issued in Japanese Application 2006-095962 on Aug. 9, 2011, with English Translation.
*Sensory Evaluation Techniques*, 4th Ed., M. Meilgaard, et al., Eds., CRC Press, Boca Raton, 2007, pp. 194-195.
Office Action issued Mar. 21, 2012, in Japanese Patent Application No. 095962/2006 (with English Translation).

* cited by examiner

*Primary Examiner* — David J Blanchard
*Assistant Examiner* — Sarah Chickos
(74) *Attorney, Agent, or Firm* — Oblon, Spivak, McClelland, Maier & Neustadt, L.L.P.

(57) ABSTRACT

Cosmetic powders which contain an N-mono long chain acyl basic amino acid and a particular α-aminolactam derivative are superior in spreadability on the skin and affinity to the skin upon application, and the lightness and moisture of the skin after application, as well as safety.

17 Claims, No Drawings

COSMETIC POWDER

CROSS REFERENCES TO RELATED APPLICATIONS

This application claims priority to Japanese Patent Application No. 2005-100164, filed on Mar. 30, 2005, which is incorporated herein by reference in its entirety.

BACKGROUND OF THE INVENTION

1. Field of the Invention

The present invention relates to cosmetic powders comprising an N-mono long chain acyl basic amino acid and a particular α-aminolactam derivative. The present invention also relates to cosmetic compositions containing such a powder.

2. Discussion of the Background

As cosmetic compositions containing a cosmetic powder as a main ingredient, makeup products such as foundations, face powders, pressed powders, blushers, eyeliners and eyebrow liners; body care products such as body powders and baby powders; and the like are commercially available. The cosmetic powder is required to exhibit properties such as superior spreadability on and superior affinity to the slin upon application, maintenance of high lightness and high moisture of the skin after application, which prevents easy occurrence of makeup deterioration, and the like.

As a method of preventing makeup deterioration, it has been proposed to perform a surface treatment on various cosmetic particles using a fluorine compound so as to impart water repellency and oil repellency (see, JP-A-55-167209, JP-A-62-250074, JP-A-1-180811, and U.S. Pat. No. 3,632, 744). However, the obtained cosmetic powder is defective in that the spreadability on the skin upon application is generally degraded and the lightness and moisture of the skin is strikingly lost after application, as compared to a cosmetic powder free of the treatment with a fluorine compound.

Also, there has been proposed a method of compounding an N-mono long chain acyl basic amino acid as a cosmetic powder and a method of improving texture of another powder or imparting a hydrophobic property on a hydrophilic surface with the use of an N-mono long chain acyl basic amino acid as a surface treatment agent (see, JP-A-61-10503). Although the N-mono long chain acyl basic amino acid is superior in spreadability on the skin upon application, it is pointed out to be defective in that, due to poor oil repellency, the lightness and moisture of the skin decreases after application, and the like.

Accordingly, it has been proposed to improve the lightness and moisture of the skin after application and to prevent makeup deterioration by performing a surface treatment on various cosmetic powders using an acyl basic amino acid and ester phosphate having a specific perfluoroalkyl group (see, JP-A-5-339126). However, the lightness and moisture of the skin after application remains unsatisfactory, and what is worse, the use of a halogen compound gave rise to a new environmental problem.

Thus, there remains a need for cosmetic powders which do not suffer from the above-described drawbacks. There also remains a need for cosmetic compositions which contain such a powder.

SUMMARY OF THE INVENTION

Accordingly, it is one object of the present invention to provide novel cosmetic powders.

It is another object of the present invention to provide novel cosmetic powders, which are superior in spreadability on the skin.

It is another object of the present invention to provide novel cosmetic powders, which provide affinity to the skin upon application.

It is another object of the present invention to provide novel cosmetic powders, which provide a sense of lightness and moisture of the skin after application.

It is another object of the present invention to provide novel cosmetic powders, which are superior in regard to environmental aspects.

It is another object of the present invention to provide novel cosmetic compositions which contain such a cosmetic powder.

These and other objects, which will become apparent during the following detailed description, have been achieved by the inventors' discovery that such a cosmetic powder can be obtained by adding an N-mono long chain acyl basic amino acid and a particular α-aminolactam derivative.

Thus, the present invention provides the following:

(1) A cosmetic powder, comprising:
(i) at least one N-mono long chain acyl basic amino acid; and
(ii) at least one α-aminolactam derivative represented by formula (1):

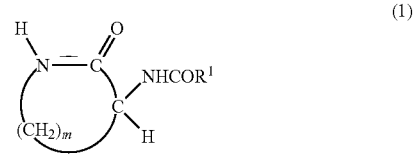

wherein $R^1$ represents a straight chain or branched chain saturated alkyl group having 2 to 30 carbon atoms, and m represents an integer of 1 to 9.

(2) The cosmetic powder according to item (1), wherein a content ratio of the at least one α-aminolactam derivative represented by formula (1) with respect to a total amount of the at least one N-mono long chain acyl basic amino acid and the at least one α-aminolactam derivative is from 0.01 wt % to 10 wt %.

(3) The cosmetic powder according to item 1 or 2, wherein the at least one N-mono long chain acyl basic amino acid is Nε-lauroyl-lysine.

(4) The cosmetic powder according to any one of items 1 to 3, wherein the at least one α-aminolactam derivative is L-α-amino-ε-caprolactam lauric acid amide.

(5) A cosmetic composition comprising any one of the cosmetic powders defined in items 1 to 4.

According to the present invention, a cosmetic powder which is superior in spreadability on the skin and affinity to the skin upon application and the lightness and moisture of the skin after application, as well as in environmental aspects can be obtained. Moreover, a cosmetic composition which is superior in spreadability on the skin and affinity to the skin upon application and the lightness and moisture of the skin after application, which provides a superior effect of preventing makeup deterioration caused by sweat, sebum, and the like (i.e., provides a makeup long lasting effect) can also be obtained.

DETAILED DESCRIPTION OF THE PREFERRED EMBODIMENTS

Hereinafter, the N-mono long chain acyl basic amino acid to be used in the present invention will be described in detail.

Examples of the amino acid forming the N-mono long chain acyl basic amino acid include basic amino acids such as lysine, ornithine, α,γ-diamino lactic acid, arginine, histidine, and the like.

Examples of the long chain acyl group include saturated or unsaturated straight chain or branched chain aliphatic acyl groups having 8 to 22 carbon atoms, and the long chain acyl group may be of a single chain length or a combined chain length. Specific examples of the long chain acyl group include 2-ethylhexanoyl, capryloyl, caproyl, lauroyl, myristoyl, parmitoyl, stearoyl, isostearoyl, oleoyl, behenoyl, cocoyl, tallowate acyl, hydrogenated tallowate acyl, and the like.

A binding site of the long chain acyl group to the basic amino acid is an amino group in the a position or an amino group in the ω position, and the binding site is limited to the amino group in the a position in the case of arginine and histidine.

Therefore, examples of the N-mono long chain acyl basic amino acid to be used in this invention are Nε-2-ethylhexanoyl-lysine, Nε-lauroyl-lysine, Nε-cocoyl-lysine, Nε-palmitoyl-lysine, Nε-isostearoyl-lysine, Nε-hydrogenated tallowate acyl lysine, Nα-capryloyl-lysine, Nα-lauroyl-lysine, Nα-myristoyl-lysine, Nα-oleoyl-lysine, Nα-behenoyl-lysine, Nδ-cocoyl-ornithine, Nδ-stearoyl-ornithine, Nδ-hydrogenated tallowate acyl ornithine, Nα-2-ethylhexanoyl-ornithine, Nα-lauroyl-ornithine, Nα-isostearoyl-ornithine, Nγ-palmitoyl-α,γ-diaminobutyric acid, Nα-hydrogenated tallowate acyl-α,γ-diaminobutyric acid, Nα-caproyl-arginine, Nα-lauroyl-arginine, Nα-parmitoyl-arginine, Nα-hydrogenated tallowate acyl arginine, Nα-cocoyl-histidine, Nα-isostearoyl-histidine, and the like. They can be used alone or in a mixture of two or more kinds thereof. Since affinity to the skin is more preferable, Nε-2-ethylhexanoyl-lysine, Nε-lauroyl-lysine and Nε-cocoyl-lysine are preferable, and Nε-lauroyl-lysine is particularly preferable.

It is possible to synthesize the α-aminolactam derivative represented by the general formula (1) by a method of converting an α-amino group of α-aminolactam obtainable through a dehydration reaction of specific amino acid into an aliphatic amide group by reacting the α-aminolactam with a saturated aliphatic acid having 3 to 31, preferably 7 to 19, more preferably 9 to 17 carbon atoms and/or its derivative.

Specific examples of the α-aminolactam include α-amino-ε-caprolactam obtainable from lysine, 3-amino-2-piperidone obtainable from ornithine, 3-amino-2-piroridone obtainable from 2,4-diaminobutanoic acid, and the like. Among the above, α-amino-ε-caprolactam is particularly preferably used. The α-aminolactam may be optically active or racemic. It is preferably an optically active form, and more preferably an L form.

Specific examples of the saturated aliphatic acid or its derivative to be used for the conversion of the α-amino group of the α-aminolactam into the aliphatic amide group include octanoic acid, pelargonic acid, capric acid, undecylic acid, lauric acid, tridecylic acid, myristic acid, pentadecylic acid, palmitinic acid, heptadecylic acid, stearic acid, arachidic acid, 2-ethylhexanoic acid, 3,5,5-trimethylhexanoic acid, isomyristic acid, isopalmitinic acid, acid chlorides corresponding to these saturated aliphatic acids, and the like. These saturated aliphatic acids or derivatives may be used alone or in combination of two or more.

The method of reacting the α-aminolactam with the saturated aliphatic acid and/or its derivative is not particularly limited, and it is possible to employ conventional amidation methods such as the amidation method disclosed in JP-A-10-265761. For example, the reaction of α-aminolactam with saturated aliphatic acid and/or its derivative may be performed in an inert solvent in the absence or the presence of catalyst such as a condensing agent. The reaction temperature is ordinarily from 10° C. to 120° C., and the reaction time is ordinarily from 0.5 hour to 48 hours. In the case where unreacted materials or the solvent is mixed with a reaction product, a purification process such as a distillation under reduced pressure, solvent separation, and recrystallization may be performed.

It is possible to obtain the powder to be used in this invention, which contains the N-mono long chain acyl basic amino acid and the α-aminolactam derivative, by a method of synthesizing the N-mono long chain acyl basic amino acid and the α-aminolactam derivative separately followed by dry mixing at a desired ratio; a method of dissolving the α-aminolactam derivative into an organic solvent, adding the N-mono long chain acyl basic amino acid, followed by distilling away the organic solvent by heating; or a method of cyclodehydrating the basic amino acid by heating to form α-aminolactam, mixing the α-aminolactam with the basic amino acid at a predetermined ratio, adding equimolar aliphatic acid, followed by a reaction in an inert solvent in the absence of catalyst. Though the reaction may be conducted in the presence of catalyst such as a condensing agent when so required, the powder preparation method of this invention is not particularly limited, and it is possible to employ an industrially advantageous method with reference to methods disclosed in JP-A-10-265761, JP-B-51-28610, and the like.

The powder to be used in this invention, which contains the N-mono long chain acyl basic amino acid and the α-aminolactam derivative, may be used in combination with a different powder used for a cosmetic composition.

The different powder is not particularly limited insofar as it is ordinarily used for cosmetic compositions, and examples thereof include inorganic powders of silicic acid, silicic acid anhydride, magnesium silicate, talc, cerisite, mica, kaolin, colcothar, clay, bentonite, titanium coated mica, bismuth oxychloride, zirconium oxide, magnesium oxide, zinc oxide flower, titanium oxide, aluminum oxide, calcium sulfate, barium sulfate, magnesium sulfate, calcium carbonate, magnesium carbonate, iron oxide, verditer, chromium oxide, chromium hydroxide, calamine, carbon black, composites thereof, and the like; an organic powder of polyamide, polyester, polyethylene, polypropylene, polystyrene, polyurethane, a vinyl resin, an urea resin, a phenol resin, a fluorine resin, a silicon resin, an acryl resin, a melamine resin, an epoxy resin, a polycarbonate resin, a divinylbenzene/styrene copolymer, a silk powder, cellulose, CI pigment yellow, CI pigment orange, and the like; composites of these inorganic powders and organic powders; and the like. These powders may be used alone or in combination of two or more.

The shape of the powder is not particularly limited, and it is possible to use a flat powder, a block powder, a flake powder, a spherical powder, or the like irrelevant from the presence/absence of pores. Among the above, the flat or spherical powder is particularly preferred. Though a primary particle diameter is not particularly limited insofar as the powder shape is maintained, the primary particle diameter is preferably from 0.01 to 80 μm, particularly form 0.1 to 20 μm, in view of the comfort and the like.

It is possible to use the powder to be used in this invention, which contains the N-mono long chain acyl basic amino acid and the α-aminolactam derivative, not only in combination with the above-described different powders but also as a surface modifier for the different powders. As a method for such usage, it is possible to employ either one of a dry type method, which is a direct treatment, and a wet type method using an appropriate solvent.

The dry type method is a convenient and effective method with which a combined powder whose surfaces are modified is readily obtained by mixing a fine particles of the powder containing the N-mono long chain acyl basic amino acid and the α-aminolactam derivative with the object power to be surface-modified with stirring or by pulverizing the powder mixture. In the case of employing the wet type method, in view of the fact that the powder containing the N-mono long chain acyl basic amino acid and the α-aminolactam derivative is hardly dissolved into nearly neutral water and an ordinary oil, it is possible to obtain a surface-treated powder by dissolving the N-mono long chain acyl basic amino acid and the α-aminolactam derivative into a solvent using calcium chloride as a solubilizing agent, contacting the solution with the different powder, washing the powder with water, eliminating the calcium chloride, and drying.

Also, it is possible to perform the surface treatment by employing methods other than the dry type and wet type methods, i.e. by dissolving the N-mono long chain acyl basic amino acid and the α-aminolactam derivative in an aqueous acidic or alkaline solvent or acidic or alkaline water, contacting the solution with the different powder, neutralizing to a nearly neutral level to precipitate the powder on the different powder, eliminating salt generated by the neutralization by washing with water, and drying.

In the cosmetic powder of the present invention, the lower limit of the content of the α-aminolactam derivative in the total amount of the N-mono long chain acyl basic amino acid and the α-aminolactam derivative is ordinarily 0.01 wt %. When the content is less than 0.01 wt %, it is difficult to achieve a satisfactory effect of the α-aminolactam derivative in improving the affinity to the skin upon application of the N-mono long chain acyl basic amino acid and moistness of the skin after application thereof. Since a stable improving effect on the affinity to the skin upon application and the moistness of the skin after application can be achieved, the lower limit of the content is preferably 0.02 wt %, more preferably 0.03 wt %, yet more preferably 0.1 wt %, still more preferably 0.3 wt %, particularly preferably 0.5 wt %, most preferably 1 wt %.

In the cosmetic powder in this invention, the upper limit of the content of the α-aminolactam derivative in the total amount of the N-mono long chain acyl basic amino acid and the α-aminolactam derivative is ordinarily 15 wt %, preferably 10 wt %. When the content exceeds the 15 wt %, the spreadability on the skin upon application and lightness of the skin after application tend to deteriorate. Since stable spreadability on the skin upon application and lightness of the skin after application can be maintained, the upper limit of the content is more preferably 5 wt %, particularly preferably 3 wt %.

In the case of using the powder containing the N-mono long chain acyl basic amino acid and the α-aminolactam derivative as a surface treatment agent for a different powder, the treatment amount is preferably from 0.1 to 30 wt %, more preferably from 0.5 to 15 wt %, with respect to the different powder. It is difficult to achieve a satisfactory modification effect when the treatment amount is less than 0.1 wt %, and the modification effect is not improved when the treatment amount exceeds 30 wt % and the use of more than 30 wt % fails to be economic.

Hereinafter, the cosmetic composition containing the powder of this invention will be described in detail.

Examples of the cosmetic composition of this invention include a basic cosmetic composition such as a lotion, an emulsion, a cream, and an oil; a makeup cosmetic composition such as a foundation, a pressed powder, a face powder, a blusher, an eyeliner, an eyebrow liner, and a mascara; a body care cosmetic composition such as a body powder, a baby powder, and an antiperspirant; a face mask; a cleanser; and the like.

The content of the powder in the cosmetic composition may be decided depending on the type of desired cosmetic composition, and is generally within the range of 0.1 to 99 wt %, based on the total weight of the composition. An ingredient, which is contained in ordinary cosmetic compositions, may be added to the cosmetic composition of the present invention in addition to the above-described essential ingredients when so required. Examples of the ingredient to be added include a solid/semisolid oil such as petrolatum, lanoline, ceresin, microcrystalline wax, carnauba wax, candellila wax, higher aliphatic acid, and higher alcohol; a liquid oil such as squalane, liquid paraffin, ester oil, diglyceride, triglyceride, and silicon oil; a fluorine-based oil such as perfluoropolyether, perfluorodecaline, and perfluorooctane; water-soluble polymer and oil-soluble polymers; a surfactant; inorganic and organic pigments; inorganic and organic pigments treated with silicon or a fluorine compound; a coloring material such as an organic dye; ethanol; an anticorrosion agent; an antioxidant; a dye; a thickener; a pH adjuster; a fragrant material; an ultraviolet ray absorber; a moisturizer; a blood circulation promoter; a coolant; an antiperspirant; a disinfectant; a skin activating agent; and the like, and they are used insofar as they do not spoil the object of this invention.

The cosmetic composition of this invention is obtainable by employing a conventional method except for mixing the powders as described in the foregoing.

Other features of the invention will become apparent in the course of the following descriptions of exemplary embodiments which are given for illustration of the invention and are not intended to be limiting thereof.

EXAMPLES

Preparation Example 1

Synthesis of L-α-amino-ε-caprolactam lauric acid amide was conducted in accordance with the method disclosed in JP-A-10-265761. 39 mmol of L-α-amino-ε-caprolactam and 58 mmol of triethylamine were added to 100 ml of dichloromethane, followed by stirring. Then, 39 mmol of lauric acid chloride was dripped into the mixture at a slow rate, and stirring was performed for 7 hours at room temperature. After that, the thus-generated precipitate was removed by filtration, and the solvent was removed by distillation, followed by recrystallization of the thus-obtained solid matter with ethyl acetate, thereby obtaining 8.8 g of L-α-amino-ε-caprolactam lauric acid amide.

Example 1

In a 1000 ml round-bottom flask, 0.1 g of L-α-amino-ε-caprolactam lauric acid amide and 500 ml of ethanol were dissolved with heating to 65° C. To the flask, 199.8 g of Nε-lauroyl-lysine was added, followed by distilling away ethanol by reducing pressured with heating, thereby obtaining a powder containing 0.05 wt % of L-α-amino-ε-caprolactam lauric acid amide with respect to a total amount of Nε-lauroyl-lysine and L-α-amino-ε-caprolactam lauric acid amide. The L-α-ammo-ε-caprolactam lauric acid amide of Preparation Example 1 and Amihope LL (commercially available Nε-lauroyl-lysine produced by Ajinomoto Co., Inc.) were used in this Example.

Examples 2 to 6 and Comparative Example 1

Powders each containing L-α-amino-ε-caprolactam lauric acid amide in the amount shown in Table 1 with respect to a total amount of NE-lauroyl-lysine and L-α-amino-ε-caprolactam lauric acid amide were prepared in the same manner as in Example 1.

Evaluation Method.

Spreadability on and affinity to the skin upon application, and the lightness and moisture of the skin after application (30 minutes later) were evaluated by 5 technical panelists based on the following evaluation criteria. For each of the evaluation items, an average value of evaluation points of the 5 panelists was calculated, and D was given to the average value less than 2, C was given to the average value of 2 to less than 3, B was given to the average value of 3 to less than 4, and A was given to the average value of 4 to 5. The results are shown in Table 1.

Spreadability on the skin upon application:
5 points: very good spreading
4 points: good spreading
3 points: moderate
2 points: somewhat poor spreading
1 point: very poor spreading Affinity to the skin upon application:
5 points: very good affinity to the skin
4 points: rather good affinity to the skin
3 points: moderate
2 points: rather poor affinity to the skin
1 point: very poor affinity to the skin Lightness of the skin after application:
5 points: very light
4 points: rather light
3 points: moderate
2 points: creaky
1 point: very creaky Moisture of the skin after application:
5 points: highly moisturized
4 points: moisturized
3 points: moderate
2 points: somewhat sticky
1 point: very sticky lightness and moisture of the skin after application, and the effects were recognized even when the content was 0.05 wt %.

Formulation Example 1

10 wt % of the powder of Example 3, 30.7 wt % of cerisite, 25.0 wt % of talc, 30.0 wt % of mica, 0.1 wt % of colcothar, 4.0 wt % of fluid paraffin, 0.1 wt % of methyl paraffin, and 0.1 wt % of a fragrant material were prepared to have the total amount of 30 g, were pulverized and mixed in a mortar and then mixed by using a small henschel mixer. The thus-obtained mixture was press molded by using a small press molding machine to obtain a sample.

Formulation Examples 2 and 3 and Comparative Formulation Example 1

Samples having compositions shown in Table 2 were prepared in the same manner as in Formulation Example 1 and evaluated by technical panelists based on the following evaluation method. The results are shown in Table 2.

Evaluation Method.

Sensory assessment of the above-described Formulation Examples and Comparative Formulation Example was conducted by 10 technical panelists to evaluate comfort during application (spreadability on and affinity to the skin), comfort (lightness and moisture of the skin) after application (30 minutes later), and makeup long lasting effect (3 hours later) according to the following evaluation criteria. For each of the evaluation items, an average value of evaluation points of the 10 panelists was calculated, and D was given to the average value less than 2, C was given to the average value of 2 to less than 3, B was given to the average value of 3 to less than 4, and A was given to the average value of 4 to 5. The results are shown in Table 2.

Comfort upon application:
5 points: very good
4 points: good
3 points: moderate
2 points: somewhat poor
1 point: poor Comfort after application:
5 points: very good
4 points: good
3 points: moderate

TABLE 1

| | | Ex. 1 | Ex. 2 | Ex. 3 | Ex. 4 | Ex. 5 | Ex. 6 | Comp. Ex. 1 |
|---|---|---|---|---|---|---|---|---|
| Nε-lauroyl-lysine (wt %) | | 99.95 | 99.9 | 98.5 | 97.0 | 90 | 85 | 100 |
| L-α-amino-ε-caprolactam lauric acid amide (wt %) | | 0.05 | 0.1 | 1.5 | 3.0 | 10 | 15 | 0 |
| upon application | Spreadability on the skin | A | A | A | A | A | B | B |
| | Affinity to the skin | B | B | A | A | A | A | C |
| after application | Lightness of the skin | A | A | A | A | B | B | C |
| | Moisture of the skin | B | A | A | A | A | A | D |

As is apparent from the results, Nε-lauroyl-lysine containing L-α-amino-s-caprolactam lauric acid amide improved spreadability on and affinity to the skin upon application, and 2 points: somewhat poor
1 point: poor Makeup long lasting effect:
5 points: very good 4 points: good
3 points: moderate
2 points: somewhat poor
1 point: poor

TABLE 2

|  | Formulation Ex. 1 | Formulation Ex. 2 | Formulation Ex. 3 | Comparative Formulation Ex. 1 |
| --- | --- | --- | --- | --- |
| Powder of Ex. 2 (wt %) | 10.0 | — | — | — |
| Powder of Ex. 4 (wt %) | — | 10.0 | — | — |
| Powder of Ex. 6 (wt %) | — | — | 10.0 | — |
| Powder of Comp. Ex. 1 (wt %) | — | — | — | 10.0 |
| Cerisite (wt %) | 30.7 | 30.7 | 30.7 | 30.7 |
| Talc (wt %) | 25.0 | 25.0 | 25.0 | 25.0 |
| Mica (wt %) | 30.0 | 30.0 | 30.0 | 30.0 |
| Colcothar (wt %) | 0.1 | 0.1 | 0.1 | 0.1 |
| Fluid Paraffin (wt %) | 4.0 | 4.0 | 4.0 | 4.0 |
| Methyl Paraffin (wt %) | 0.1 | 0.1 | 0.1 | 0.1 |
| Fragrant Material (wt %) | 0.1 | 0.1 | 0.1 | 0.1 |
| Comfortableness upon application | A | A | A | C |
| Comfortableness after application | A | A | A | D |
| Makeup long lasting effect | B | A | A | C |

As is apparent from Table 2, it was revealed that the samples (pressed face powders) of this invention are more excellent in makeup long lasting effect, comfortableness upon application, and comfortableness after application as compared to the comparative sample.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A cosmetic powder, comprising:
   (i) Nε-lauroyl-lysine; and
   (ii) α-amino-ε-caprolactam lauric acid amide,
   wherein said α-amino-ε-caprolactam lauric acid amide is present in an amount of from 0.02 wt % to 15 wt %, with respect to a total amount of said Nε-lauroyl-lysine and said α-amino-ε-caprolactam lauric acid amide,
   wherein the cosmetic powder is oil-free.

2. A cosmetic composition, which is prepared by mixing a cosmetic powder according to claim 1 and at least one cosmetically acceptable ingredient.

3. The cosmetic composition according to claim 2, which comprises mixing said cosmetic powder in an amount of 0.1 to 99 wt %, based on the total weight of the composition.

4. A cosmetic composition according to claim 2, wherein said at least one cosmetically acceptable ingredient is at least one member selected from the group consisting of a water-soluble polymer, an oil-soluble polymer, a surfactant, an inorganic pigment, an organic pigment, an inorganic pigment treated with a silicon compound, an inorganic pigment treated with a fluorine compound, an organic pigment treated with a silicon compound, an organic pigment treated with a fluorine compound, ethanol, an anticorrosion agent, an antioxidant, a dye, a thickener, a pH adjuster, a fragrant material, an ultraviolet ray absorber, a moisturizer, a blood circulation promoter, a coolant, an antiperspirant, a disinfectant, a skin activating agent, and mixtures thereof.

5. A method of preparing a surface-treated powder, comprising:
   (a) mixing a powder with a cosmetic powder according to claim 1.

6. The method of claim 5, wherein said powder is at least one member selected from the group consisting of a powder of silicic acid, a powder of silicic acid anhydride, a powder of magnesium silicate, a powder of talc, a powder of cerisite, a powder of mica, a powder of kaolin, a powder of colcothar, a powder of clay, a powder of bentonite, a powder of titanium coated mica, a powder of bismuth oxychloride, a powder of zirconium oxide, a powder of magnesium oxide, a powder of zinc oxide flower, a powder of titanium oxide, a powder of aluminum oxide, a powder of calcium sulfate, a powder of barium sulfate, a powder of magnesium sulfate, a powder of calcium carbonate, a powder of magnesium carbonate, a powder of iron oxide, a powder of verditer, a powder of chromium oxide, a powder of chromium hydroxide, a powder of calamine, a powder of carbon black, a powder of polyamide, a powder of polyester, a powder of polyethylene, a powder of polypropylene, a powder of polystyrene, a powder of polyurethane, a powder of a vinyl resin, a powder of an urea resin, a powder of a phenol resin, a powder of a fluorine resin, a powder of a silicon resin, a powder of an acryl resin, a powder of a melamine resin, a powder of an epoxy resin, a powder of a polycarbonate resin, a powder of a divinylbenzene/styrene copolymer, a silk powder, a powder of cellulose, a powder of CI pigment yellow, a powder of CI pigment orange, and mixtures thereof.

7. A surface-treated powder, comprising particles of a powder, wherein at least a portion of a surface of said particles has been coated with a cosmetic powder according to claim 1.

8. The surface-treated powder of claim 7, wherein said powder is at least one member selected from the group consisting of a powder of silicic acid, a powder of silicic acid anhydride, a powder of magnesium silicate, a powder of talc, a powder of cerisite, a powder of mica, a powder of kaolin, a powder of colcothar, a powder of clay, a powder of bentonite, a powder of titanium coated mica, a powder of bismuth oxychloride, a powder of zirconium oxide, a powder of magnesium oxide, a powder of zinc oxide flower, a powder of titanium oxide, a powder of aluminum oxide, a powder of calcium sulfate, a powder of barium sulfate, a powder of magnesium sulfate, a powder of calcium carbonate, a powder of magnesium carbonate, a powder of iron oxide, a powder of verditer, a powder of chromium oxide, a powder of chromium hydroxide, a powder of calamine, a powder of carbon black, a powder of polyamide, a powder of polyester, a powder of polyethylene, a powder of polypropylene, a powder of polystyrene, a powder of polyurethane, a powder of a vinyl resin, a powder of an urea resin, a powder of a phenol resin, a powder of a fluorine resin, a powder of a silicon resin, a powder of an acryl resin, a powder of a melamine resin, a powder of an epoxy resin, a powder of a polycarbonate resin, a powder of a divinylbenzene/styrene copolymer, a silk powder, a powder of cellulose, a powder of CI pigment yellow, a powder of CI pigment orange, and mixtures thereof.

9. The cosmetic powder according to claim 1, wherein said α-amino-ε-caprolactam lauric acid amide is present in an amount of from 0.02 wt % to 10 wt %, with respect to a total amount of said Nε-lauroyl-lysine and said α-amino-ε-caprolactam lauric acid amide.

10. The cosmetic powder according to claim 1, wherein said α-amino-ε-caprolactam lauric acid amide is present in an amount of from 0.03 wt % to 15 wt %, with respect to a total amount of said Nε-lauroyl-lysine and said α-amino-ε-caprolactam lauric acid amide.

11. The cosmetic powder according to claim 1, wherein said α-amino-ε-caprolactam lauric acid amide is present in an amount of from 0.3 wt % to 15 wt %, with respect to a total amount of said Nε-lauroyl-lysine and said α-aminoε-caprolactam lauric acid amide.

12. The cosmetic powder according to claim 1, wherein said α-amino-ε-caprolactam lauric acid amide is present in an amount of from 1 wt % to 15 wt %, with respect to a total amount of said Nε-lauroyl-lysine and said α-amino-ε-caprolactam lauric acid amide.

13. The cosmetic powder according to claim 1, wherein said α-amino-ε-caprolactam lauric acid amide is present in an amount of from 0.05 wt % to 15 wt %, with respect to a total amount of said Nε-lauroyl-lysine and said α-amino-ε-caprolactam lauric acid amide.

14. The cosmetic powder according to claim 1, wherein said α-amino-ε-caprolactam lauric acid amide is present in an amount of from 1.5 wt % to 15 wt %, with respect to a total amount of said Nε-lauroyl-lysine and said α-amino-ε-caprolactam lauric acid amide.

15. The cosmetic powder according to claim 1, wherein said α-amino-ε-caprolactam lauric acid amide is present in an amount of from 3 wt % to 15 wt %, with respect to a total amount of said Nε-lauroyl-lysine and said α-amino-ε-caprolactam lauric acid amide.

16. A method of making the cosmetic powder according to claim 1, comprising combining (i) and (ii).

17. A method of applying a cosmetic powder, comprising applying the cosmetic powder according to claim 1 to skin.

* * * * *

UNITED STATES PATENT AND TRADEMARK OFFICE
CERTIFICATE OF CORRECTION

PATENT NO. : 8,603,504 B2  Page 1 of 1
APPLICATION NO. : 11/392564
DATED : December 10, 2013
INVENTOR(S) : Sagawa et al.

It is certified that error appears in the above-identified patent and that said Letters Patent is hereby corrected as shown below:

In the Claims

Column 11, claim 11, line 25:
"...said α-aminoε-caprolactam..." should read --...said α-amino-ε-caprolactam...--

Signed and Sealed this
Fifteenth Day of July, 2014

Michelle K. Lee
*Deputy Director of the United States Patent and Trademark Office*